United States Patent [19]

Cuppy

[11] Patent Number: 5,749,857
[45] Date of Patent: May 12, 1998

[54] CATHETER SYSTEM

[76] Inventor: Michael J. Cuppy, 13805 Frontier La., Burnsville, Minn. 55337

[21] Appl. No.: 637,867

[22] Filed: Apr. 25, 1996

[51] Int. Cl.$^6$ .................................................. A61M 5/00
[52] U.S. Cl. ................ 604/164; 604/161; 604/165; 128/749
[58] Field of Search ...................... 128/749, 753, 128/754; 604/160, 161, 164, 165, 167

[56] References Cited

U.S. PATENT DOCUMENTS

| | | |
|---|---|---|
| 3,500,828 | 3/1970 | Podhora . |
| 3,670,729 | 6/1972 | Bennett et al. .............. 604/164 X |
| 3,714,945 | 2/1973 | Stanley . |
| 3,977,400 | 8/1976 | Moorehead . |
| 3,994,293 | 11/1976 | Ferro . |
| 3,995,619 | 12/1976 | Glatzer .................... 128/749 X |
| 4,106,491 | 8/1978 | Guerra . |
| 4,200,096 | 4/1980 | Charvin . |
| 4,468,224 | 8/1984 | Enzmann et al. ............ 604/164 X |
| 4,531,987 | 7/1985 | Yates ....................... 604/164 X |
| 4,549,554 | 10/1985 | Markham et al. .............. 128/753 |
| 4,735,215 | 4/1988 | Goto et al. .................. 128/754 |
| 4,828,548 | 5/1989 | Walter . |
| 4,874,373 | 10/1989 | Luther et al. . |
| 4,893,635 | 1/1990 | DeGroot et al. .............. 128/754 |
| 4,894,052 | 1/1990 | Crawford . |
| 4,907,599 | 3/1990 | Taylor ....................... 128/734 |
| 4,944,308 | 7/1990 | Akedrfeldt .............. 128/754 X |
| 4,994,042 | 2/1991 | Vadher ....................... 604/165 |
| 5,129,884 | 7/1992 | Dysarz ....................... 604/164 |
| 5,400,798 | 3/1995 | Baran ........................ 128/754 |

*Primary Examiner*—Sam Rimell
*Attorney, Agent, or Firm*—Larkin, Hoffman, Daly & Lindgren

[57] ABSTRACT

The catheter system is used to safely insert a plastic catheter into a peripheral vein of patient who needs access for fluid and/or drug therapy. The catheter has added to the normal catheter hub a secondary port Y-Port that is used to attach IV line when catheter is inserted. This Y-port also has a one-way check valve to prevent blood from backing out the Y-port before the line is attached. The terminal end of the catheter hub has a rubber stopper to prevent blood from leaking out after the needle is removed. This feature effectively closes the previously open hub of the catheter, thus allowing near-bloodless IV access and allowing the flash chamber to be located within hub. The needle also includes a vent hole that vents blood into the flash chamber. A safety tube assembly as the back half of the catheter system includes protective tube and release mechanism which functions are to spring the needle out of catheter and house the used needle safely within the telescoping tube of the needle shuttle when trigger is pressed. The push flanges on the catheter hub are for easy catheter insertion and separation of the needle from the catheter.

1 Claim, 15 Drawing Sheets

CATHETER SYSTEM

BACKGROUND OF THE INVENTION

1. Field of the Invention

The present invention is for a catheter, and more particularly, pertains to a catheter system including a catheter and a safety tube assembly.

This catheter needle is used in healthcare fields where IV catheterization is required to facilitate patient care (i.e., pre-hospital (ambulance) setting; in-hospital setting; clinic setting). Specifically, the catheter is used any place a peripheral IV site is needed in order to facilitate patient treatment using fluids and/or IV drug therapy.

All current IV catheters have to have a "Heparin Lock" attachment added to catheter hub after IV start. If this is not done quickly and correctly, there is a serious risk of blood exposure.

Some "safety catheters," while providing protection from needle punctures, have manufactured catheter packaging that is to long to fit in restrictive IV needle storage compartments (drug boxes, crash carts, etc.).

As is by now plainly evident, the current state of IV needle and blood protection is woefully inadequate; in fact, quite dangerous. The health care industry is long overdue for the enhancements found in this catheter. There is no needle currently manufactured that addresses all the dangers and deficiencies outlined above. The catheter system of the present invention either solves or eliminates all of the above mentioned deficiencies.

2. Description of the Prior Art

The standard method to start an IV is to insert the catheter into the vein, then quickly pull the needle out and discard it before one pokes himself with it, then even more quickly insert IV line into end of the catheter hub before too much blood can spill out, contaminating oneself and the patient area. The disadvantages of this old method our obvious—a high probability of sticking oneself or the patient with needle and/or exposing and contaminating oneself (AIDS, Hepatitis, hemorrhagic fevers, etc.) to blood from site. This unsafe procedure has been the standard method almost since the IV needle was first invented. This is a very dangerous technique, and has to be eliminated and replaced with a safer method due to the prevalence of deadly infectious diseases faced by healthcare professionals today.

The current method of drug injection is injecting the drug up to eight inches further back from the IV catheter (the first med port can be eight inches up the IV line), which can make or break the effectiveness of time sensitive and/or concentration sensitive drugs. Emergency medications like Adenosine (time sensitive), are less effective when injected further from the site if IV.

All other IV needles have the "blood flash chamber" located to far back on needle (where your hand screens your line of sight) resulting in concealed visualization of flash. Ones fingers and hand partially and/or totally obscure old flash chamber. This means user has to reposition hands to see if they are in the vein, this manipulation can cause the needle tip to pull out of vein and precipitate an unsuccessful IV attempt.

Many current style IV catheters do not provide any automatic protection from needle punctures. One has to manually "re-cap" needle, risking a needle stick, or set needle aside until you finish IV start, hoping one does not forget to dispose of it and/or sticking oneself prior to safe disposal. Other "safety" needles require one to manually retract needle all the way back until needle locks into protective tube. Many times, people forget to fully retract needle into locked position, allowing the needle to slip out of safety tube, again risking exposure to needle stick. Some "safety needle" designs adequately protect the user from needle punctures, but have residual blood dispersed all over proximal end of safety tube where hub seal (blood stopper) is located. All are either inadequate or unsafe designs to completely protect the user.

The newer "safety IV catheters" do not allow access to draw blood (needed for blood sample and/or blood sugar analysis) after insertion. So, in order to collect blood for analysis, one has to stick patient again and re-expose yourself and patient to the same risks associated with the first stick (blood spillage and/or needle puncture).

Current catheters do not provide an adequately designed "push flange" used for insertion of IV needle into vein after initial blood flash-back. Most are either nonexistent or too small/short/smooth to be effective, thereby reducing chances of successful catheter insertion.

All current catheters do not provide any protection from blood regurgitation up IV line when IV bag is set/dropped down. This usually causes the blood to clot and clogs the IV forcing user to discontinue IV, necessitating another IV start.

No IV currently provides a safe and blood-free method to change-out IV lines. Many times IV lines need to be replaced for various reasons, when old line is disconnected it will leak/flow blood until new line is attached. If this is not done quickly and correctly, there is a serious risk of blood exposure.

All current IV catheters do not provide any built-in protection from blood exposure if IV line is accidentally or purposefully (violent/psychotic patient) disconnected from IV catheter. If this occurs, there is a very serious blood contamination problem, as large amounts of blood can exsanguinate from patient before IV line can be either reconnected or discontinued.

SUMMARY OF THE INVENTION

The general purpose of the present invention is a catheter system with a plastic secondary lumen port (Y-port) with a rubber check valve built into its lumen. This catheter allows user to start an IV minimizing or negating exposure to blood and needle punctures. This port has seven main functions:

1. The rubber check valve is integral for effectively venting flash chamber during IV start, then sealing the chamber afterwards. This rubber valve (check valve) is used to prevent blood from exiting the catheter before and after the line is attached; it operates when the piercing needle is inserted into vein, blood then flows back through needle lumen, then out needle vent hole into flash chamber finally pushing into check valve. This blood fluid pressure pushes valve up against the valve seat, effectively closing lumen. When IV line is attached and fluid started, the hydraulic pressure of IV fluid will open check valve. The IV fluid flows around rubber valve and into the hub chamber, then into patient;

2. The check valve also, prevents back-flow of blood into IV line during standard IV use;

3. Prevents bleeding if IV line gets separated from hub;

4. Allows for safe IV line substitution;

5. The Y-port opening is positioned to point at patient. The advantages being no need to loop IV line around catheter after IV placement. This prevents the IV line from catching and/or kinking on anything and either pulling IV out or ending normal flow; and, 6. Finally, the Y-port is used to attach the IV line and run fluid into patient when the catheter is successfully inserted.

According to one embodiment of the present invention, there is provided a catheter system with a terminal end of the primary catheter port has a prepierced resealable rubber stopper to prevent blood from leaking out after steel needle is removed. The "stopper" functions by allowing a needle to easily be inserted through the prepierced rubber plug, spreading open rubber in stopper allowing access to inside of flash chamber. When Teflon coated needle is removed, the rubber re-seals itself automatically closing opening and re-establishing a fluid-tight seal. When the "stopper" is used in conjunction with the Y-port, they effectively seal the previously open hub. This allows the piercing needle to be inserted through closed chamber into catheter and allowing the venting of blood into this new flash chamber through a vent hole in piercing needle. After IV start, the prepierced resealable stopper acts to:

1. Keep chamber closed when piercing needle is removed;
2. Used as injection site for medications;
3. Site to extract blood for analysis;
4. Can be used as site for piggy-back IV.

The stopper is made of suitable high-grade rubber or polymer for the prepierced reseal injection site. The valve could be made many different ways, using existing technology.

The above two features allow the creation of a more conveniently relocated flash chamber which has now been moved to the proximal end of catheter hub (see diagram) for easy visualization of blood flash-back when piercing needle enters the vein (the current location for flash chamber is at distal end of steel piercing needle, which is a poor location). The flash-back is obtained by creating a hole in steel needle at the level of the catheter hub. This shortened flash opening will swiftly leak blood into new flash chamber catheter hub for prompt and convenient visualization of blood which signifies a successful needle insertion into vein. This new flash chamber creates two important advantages over existing IV needles:

1. Blood "flashes" quicker due to shortened travel length into the more proximally located flash chamber. This means that if patient has low blood pressure, the blood can take a longer time reaching the lengthier "old" flash chamber. On current 18 ga. piercing needles, the "length to flash chamber" (tip of needle to flash chamber opening) is 16 mm to 30 mm longer then the catheter system. If the blood flow is slow, the user could mistakenly think they have not successfully entered vein because they have not yet seen the "flash" of blood in flash chamber. The user then assumes they are not in vein (no flash) and prematurely terminates the IV start.

2. Of prime importance, visualization of "flash" now occurs up at front of catheter hub allowing an unobstructed (user's hands/fingers) view of "flash." This eliminates the movement (needle is not accidentally manipulated out of vein) currently required to visualize the flash, greatly increasing chances of successful IV start.

There are new optimized push flanges located on catheter hub for easy insertion of catheter into vein (see sketches). These exterior flanges will project laterally from proximal end of catheter flash chamber (as per diagram) and on top of terminal end of Y-port and will project out 2 mm. The distal end of flange will have edge curled back to create a lip to catch finger/fingernail on to be used to easily advance catheter into vein without unnecessary movement or slippage.

The telescoping safety tube assembly is used to safely house the used needle after IV start is complete and to contain latent blood in used needle. At the proximal end of safety housing, a built-in trigger button is incorporated to release a tensed spring that encircles the needle shuttle. This spring will automatically propel the needle shuttle into telescoping tube, the force of spring will extend tube to its full length, where auto-locking mechanism will lock the now extended protective tube in place. These features allow the user to easily push a button after the IV start and have piercing needle automatically retract into safety tube. The telescoping tube system is incorporated to minimize the size of packaged product and eliminate blood exposure from used needle. This reduction in packaged size, is especially important to storage constraints in the pre-hospital setting.

Significant aspects and features of the present invention are:

1. Protection from accidental needle puncture. This device will at the push of a button, retract needle into protective housing, eliminating chance of needle puncture to user;

2. Elimination of latent blood contamination from discarded "protective" needle tubes;

3. Provides optimum flash chamber location;

4. Assures the most proximal injection site known (similar to a "Heparin Lock") for IV medication infusion;

5. Provides site to safely draw blood for analysis (i.e., blood alcohol or blood sugar testing) without sticking patient a second time;

6. Provides a better site (new push flange) to advance catheter with thumbnail or index finger so as not to inadvertently move IV out of position prior to insertion of catheter in vein. Provides a better grip design for holding IV catheter while starting IV and places hand and fingers away from trigger release to eliminate premature/accidental needle ejection;

7. Provides safeguards against blood leakage/contamination in the event of IV line separation from catheter;

8. This device can optionally be used as a "Heparin Lock" where needed; and,

9. The overall new design will allow users to greatly increase there chances of starting the IV the first time.

10. Minimizing/eliminating blood-born contamination during IV start.

Having thus described embodiments of the present invention, it is the principal object of the present invention to provide a closed hub catheter system.

Objects of the present invention are:

1. Flash-back of blood and visualization thereof, now takes place within front of sealed hub area (in front of grip position during IV start). Current IV catheters have flash chamber located at distal end of needle, partially or totally obscuring view of flash chamber;

2. The catheter is easily inserted into vein using the larger, and more strategically placed "push flanges," improving omissions or weaknesses with other IV needles;

3. Attaching IV line will occur on the "Y" junction opening, instead of normal catheter hub opening on all other needles;

4. Due to placement of Y-port, the use will not be required to "loop" IV line, then tape in place. "Looping" is required because catheter can be pulled out of vein if the IV line routing is not reversed. Reversing causes force to push catheter into vein instead;

5. The needle is safely and automatically disposed of by pressing a button that activates a push spring to eject needle from rubber prepierced stopper, then into the protective telescoping/locking tube system where it is safely stored until disposal; and, 6. The system is a closed hub system minimizing or negating any blood exposure.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
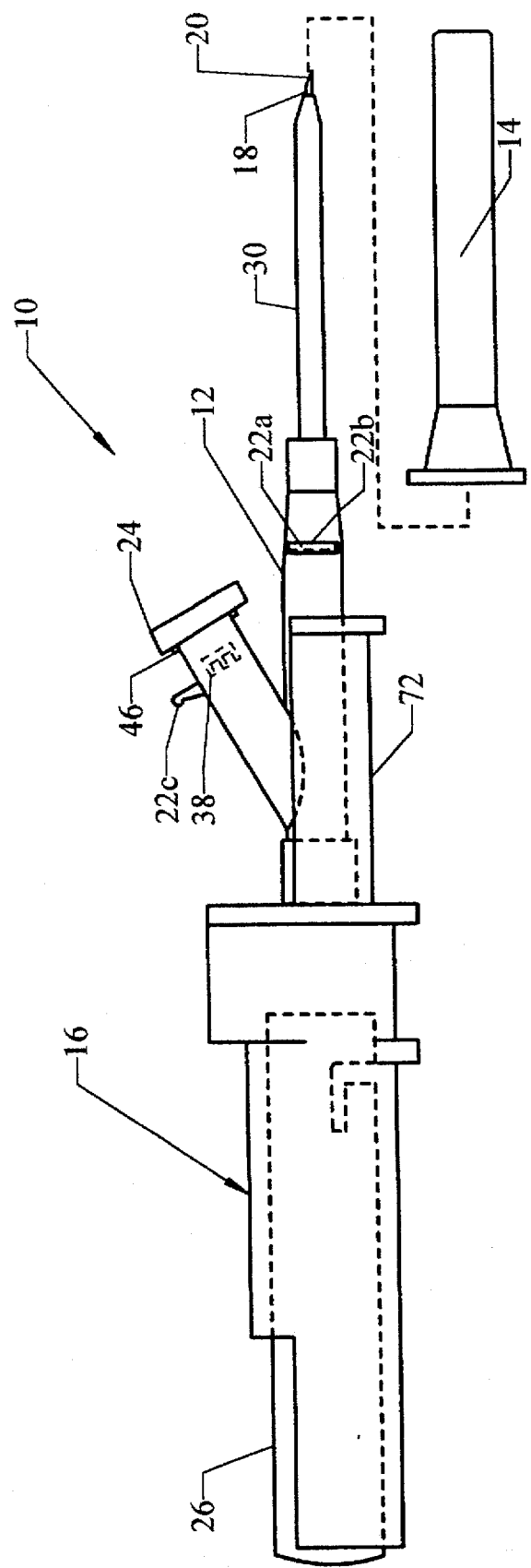
FIG. 1 illustrates a plan view of a catheter system, the present invention.

FIG. 1 illustrates a plan view of a closed hub catheter system 10, including a catheter 12, with a protective cap 14 and a safety tube or safety tube assembly 16. The catheter 12 includes a needle 18 with an angled point 20, push flanges 22a–22c, a vent cap 24, all later described in detail. The safety tube assembly 16 includes a spring biased telescoping tube 26 as later described in detail. A grip area 72 is provided for insertion. A check valve 38 is illustrated in dashed lines, as later described in detail.

Figure 2:
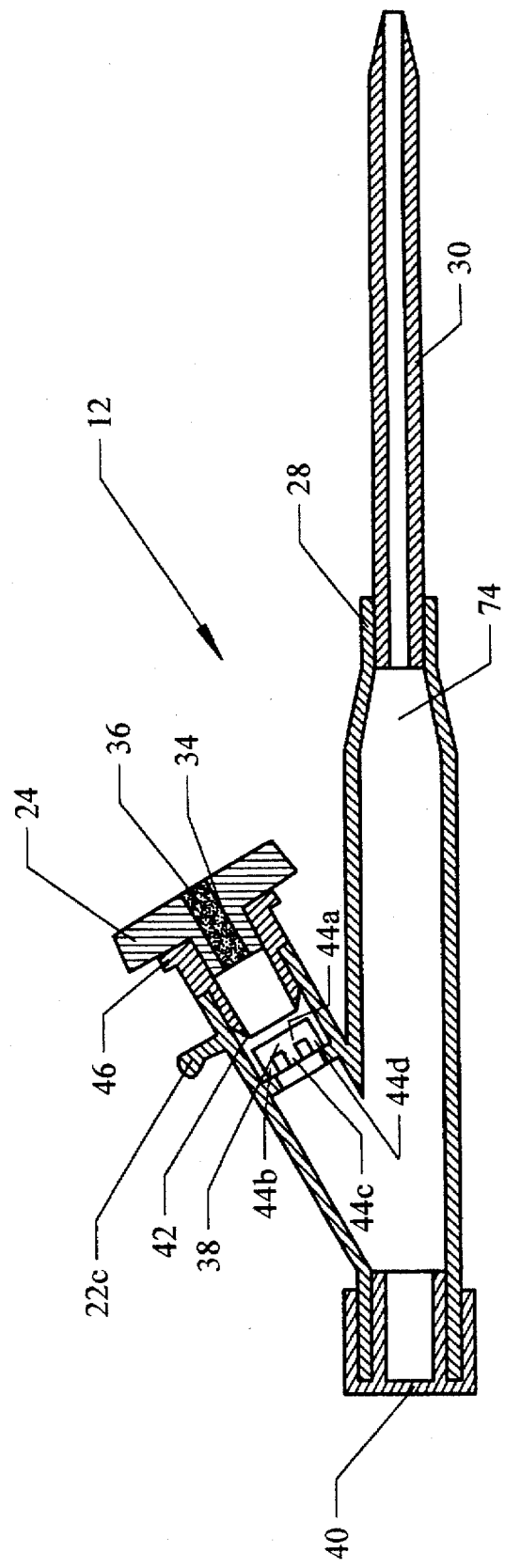
FIG. 2 illustrates a cross sectional view of the catheter.

FIG. 2 illustrates a cross sectional view of the closed hub catheter 12, where all numerals correspond to those elements previously described. A housing 28 supports a flexible catheter tube 30, a vent cap 24 with a hole 34 filled with a material, such as cotton 36 for venting air, a check valve 38 with a plurality of feet, and a polymer prepierced stopper 40. The check valve 38 rides against an inwardly extending flange 42. The check valve 38 is geometrically configured with downwardly extending feet 44a–44d for the passage of fluids between and about the feet, such as four or five. The end of the vent cap 24 forms a coupling 46 for a lure lock. A flashing chamber area 74 is provided for visualization of the blood flow.

Figure 3:
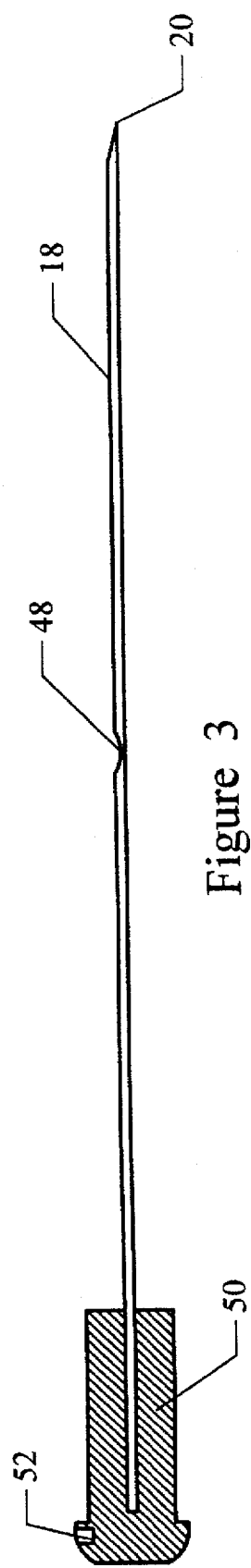
FIG. 3 illustrates a cross sectional view of the needle.

FIG. 3 illustrates a cross sectional view of the needle 18 with a geometrically configured needle carrier 50. The needle 18 includes a blood vent hole 48. The needle carrier 50 includes a pin lock hole 52, as later described in detail.

Figure 4:
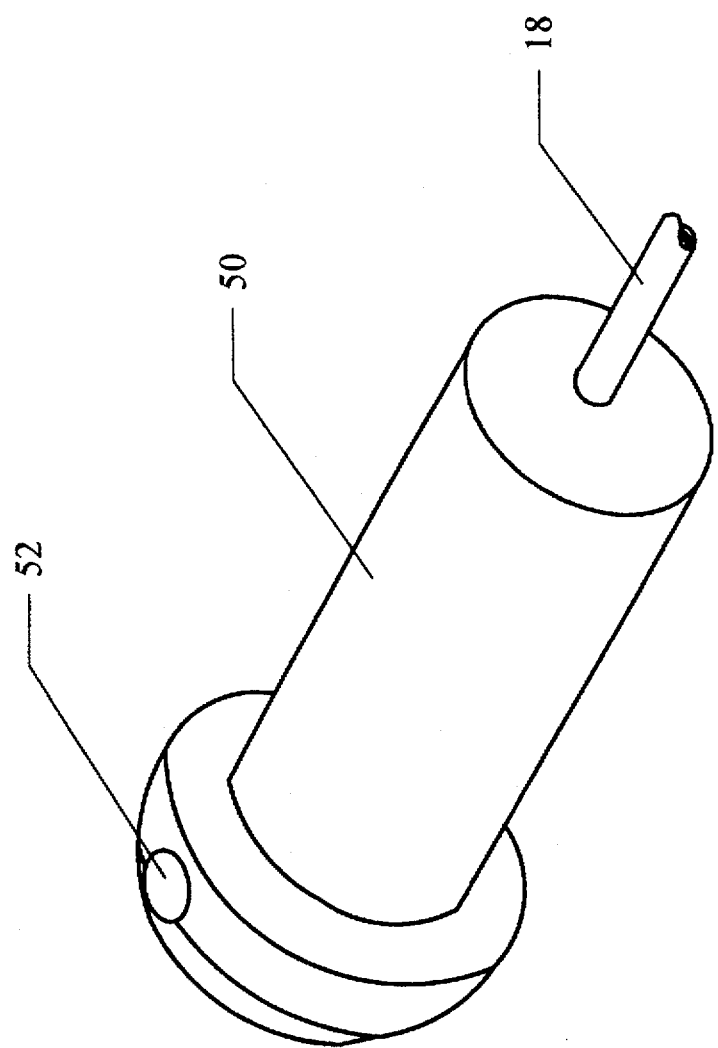
FIG. 4 illustrates an isometric view of the needle carrier.

FIG. 4 illustrates an isometric view of the needle carrier 50, where all numerals correspond to those elements previously described.

Figure 5:
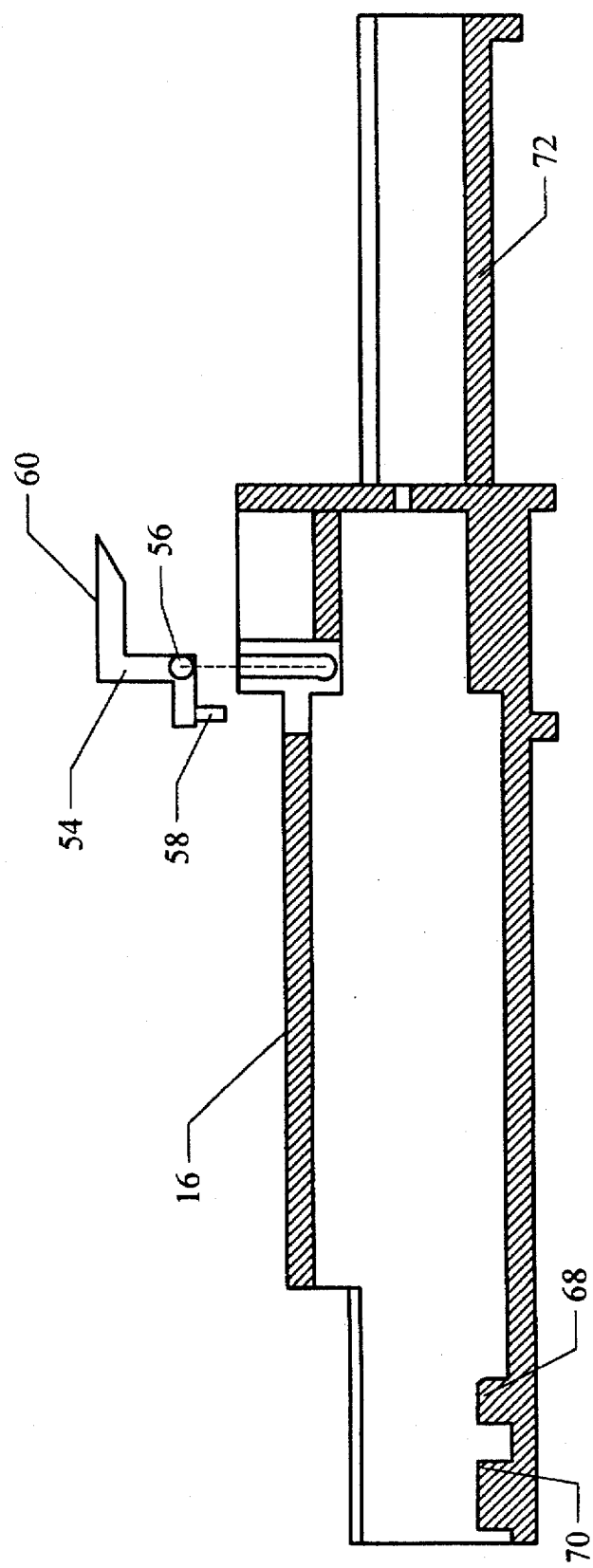
FIG. 5 illustrates a cross sectional view of the safety tube assembly and a trigger.

FIG. 5 illustrates a cross sectional view of the safety tube system 16, as later described in detail. A trigger 54 about a pivot axis 56 includes an engaging pin 58. The trigger 54 is actuated by pressing a finger against the trigger finger actuation surface 60, as later described in detail, for actuation of the spring biased needle 18 and its components into the spring biased telescoping needle tube 26.

Figure 6:
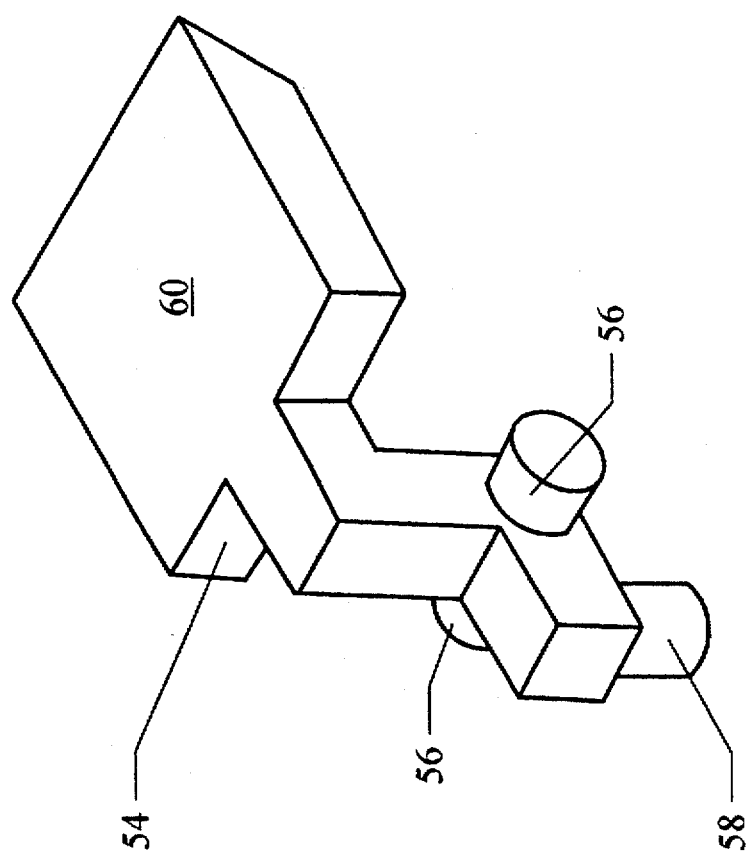
FIG. 6 illustrates an isometric view of the trigger.

FIG. 6 illustrates an isometric view of the trigger 54, where all numerals correspond to those elements previously described.

Figure 7:
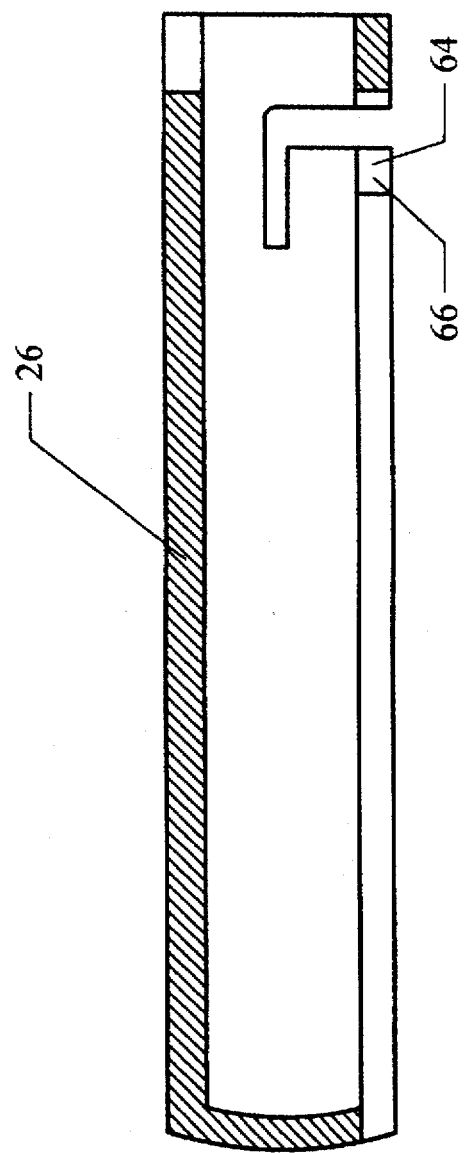
FIG. 7 illustrates a cross sectional view of a telescoping tube which engages in the safety tube assembly.

FIG. 7 illustrates a telescoping tube which is spring biased within the safety tube assembly 16, as later described in detail.

Figure 8:
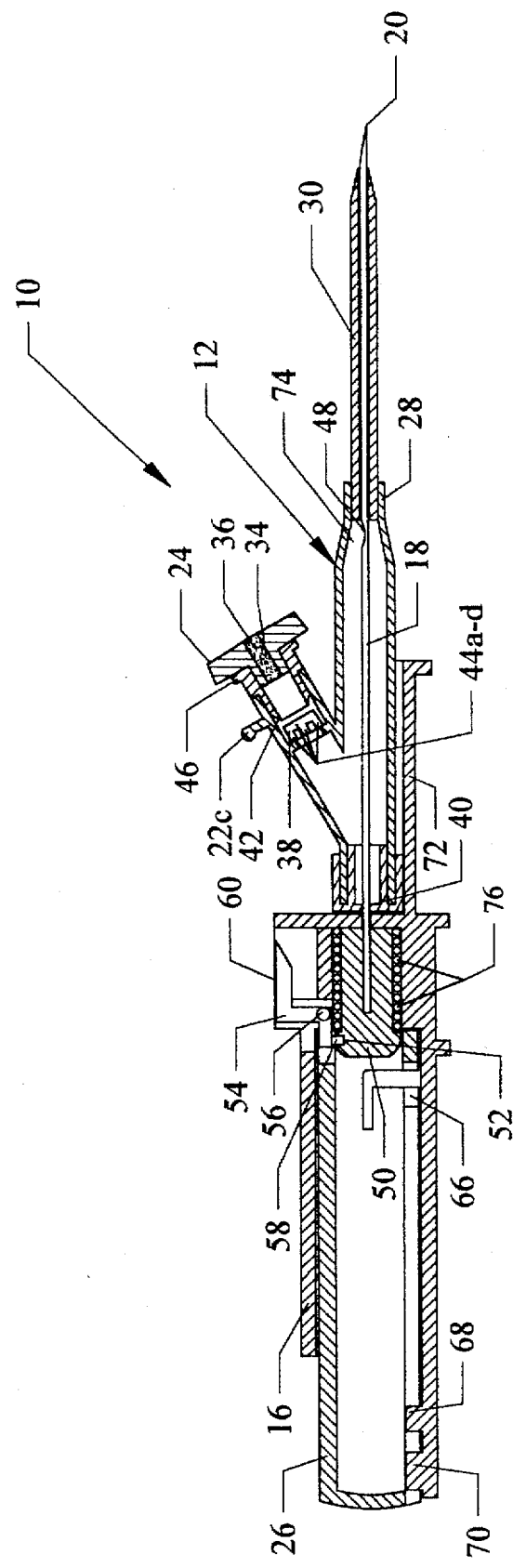
FIG. 8 illustrates a cross sectional view of the catheter of FIG. 1.

FIG. 8 illustrates a cross sectional view of the catheter system 10 prior to use, where all numerals correspond to those elements previously described. Spring 76 biases the needle carrier 50 to react with the spring biased telescoping tube 26.

Figure 9:
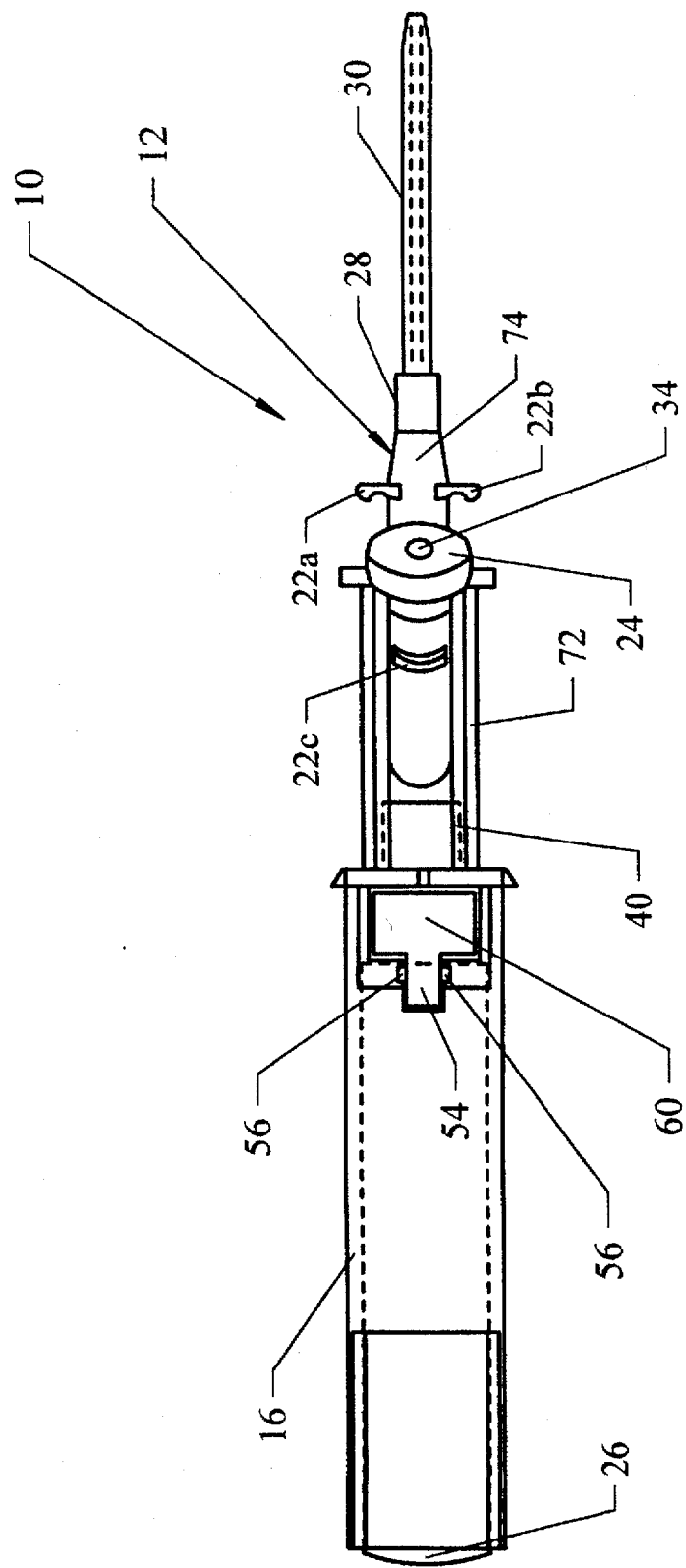
FIG. 9 illustrates a top plan view of the catheter.

FIG. 9 illustrates a top plan view of FIG. 8 corresponding to those elements previously described, and further illustrating the push flanges 22a–22c, which can be actuated, such as by a finger or even by a fingernail.

Figure 10:
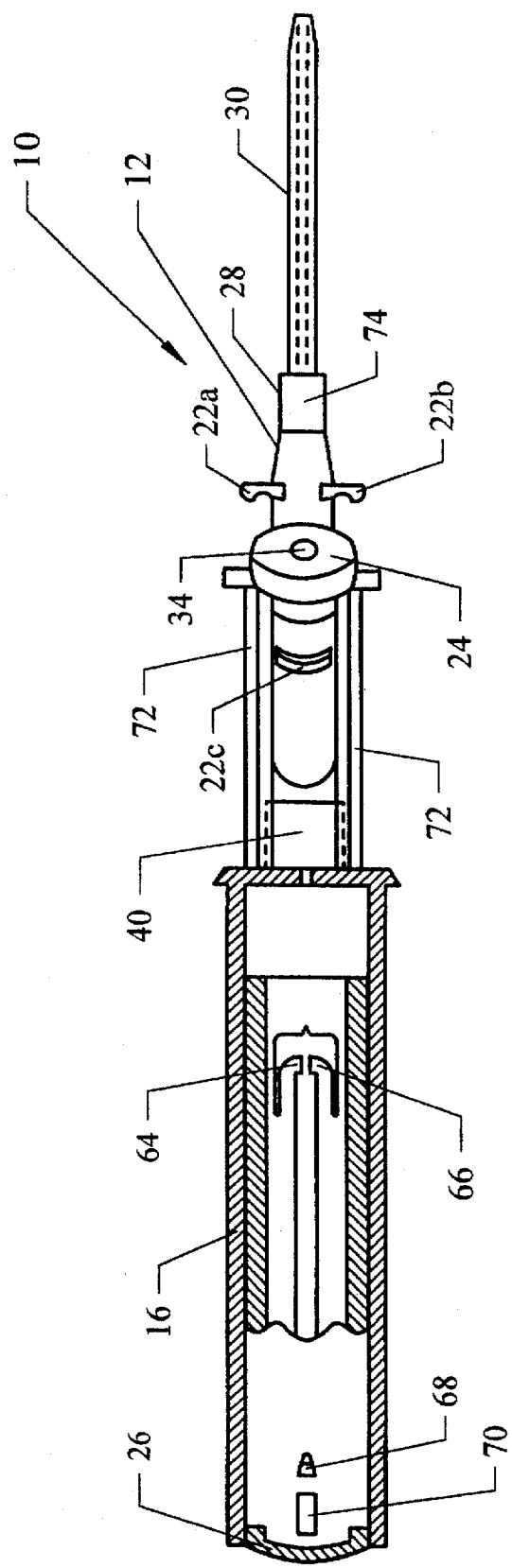
FIG. 10 illustrates a top view in partial cross section of the catheter.

FIG. 10 illustrates a top view in partial cross section the safety tube system 16 and partial cross section illustrating the telescoping tube 26 with locking arms 64 and 66, which engage over and in between a ramped wedge 68 and a locking member 70.

Figure 11:
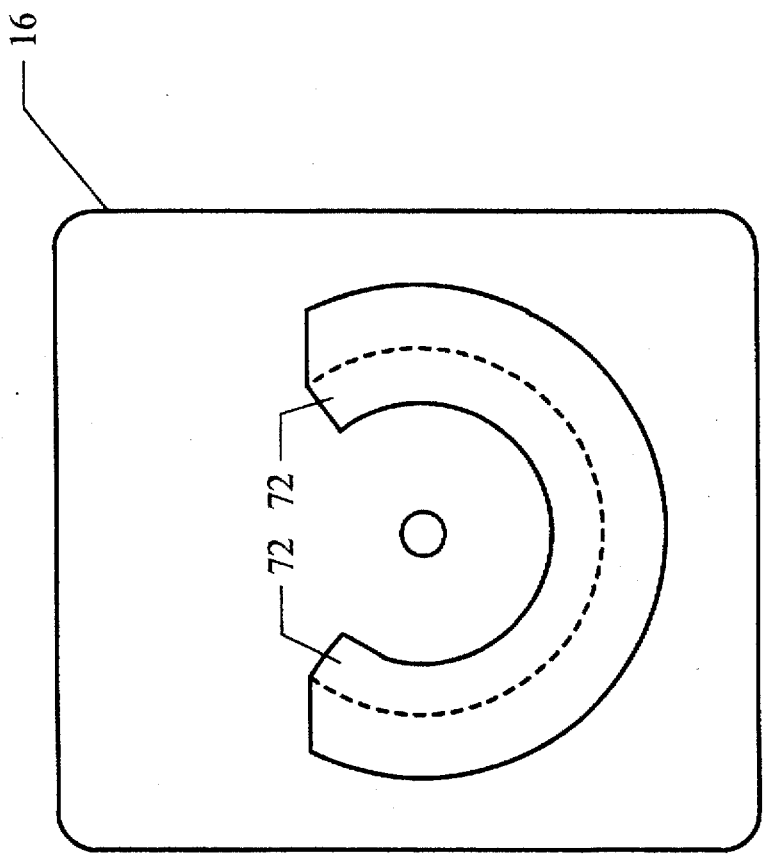
FIG. 11 illustrates a front view of the catheter system.

FIG. 11 illustrates a front view of the catheter system 10, particularly the gripping area.

Figure 12:
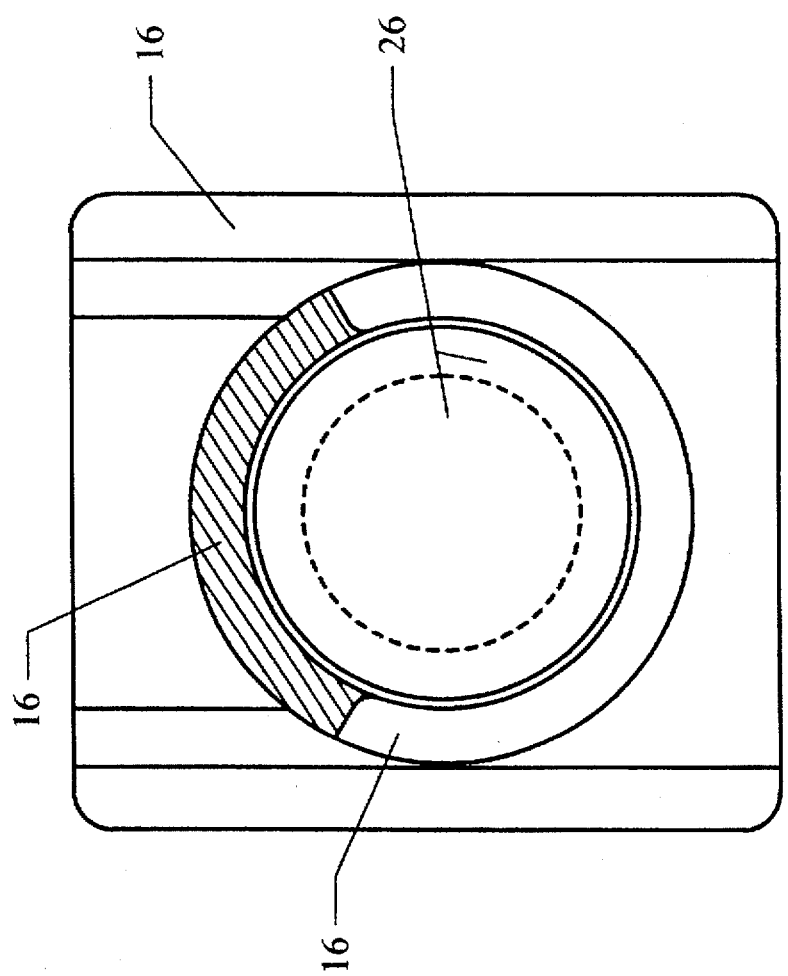
FIG. 12 illustrates a back view of the catheter system.

FIG. 12 illustrates a back view of the catheter system 10.

Figure 13:
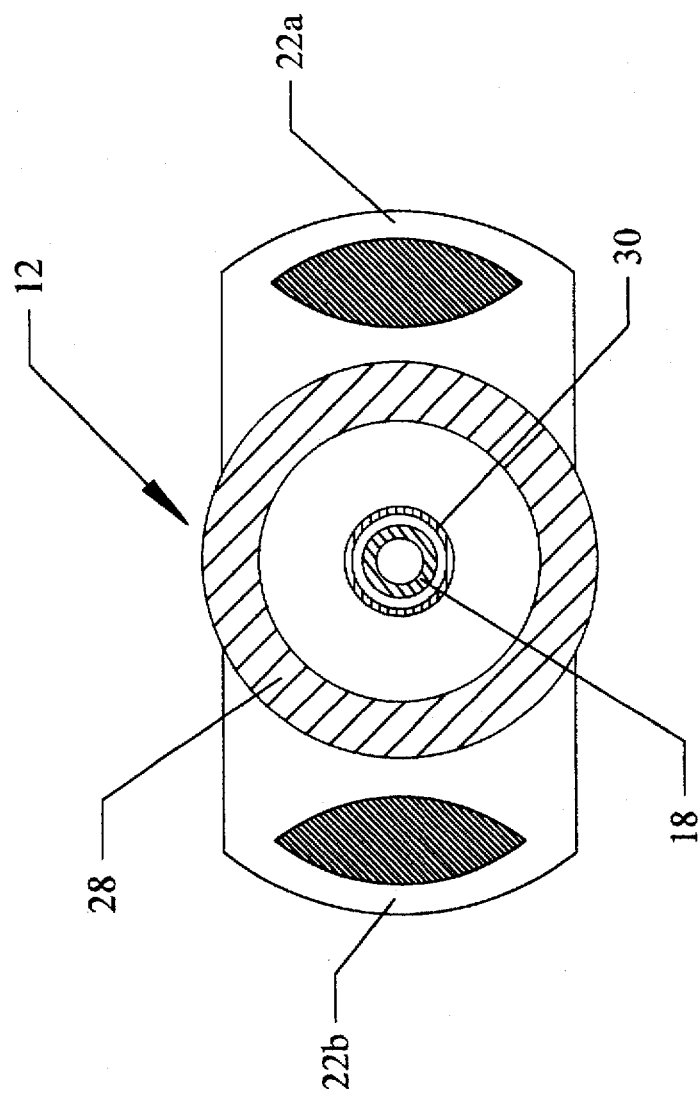
FIG. 13 illustrates a back end view of the push flanges about the Y-port which is not illustrated.

FIG. 13 illustrates a back end view illustrating the push flanges 22a and 22b.

MODE OF OPERATION

Figure 14:
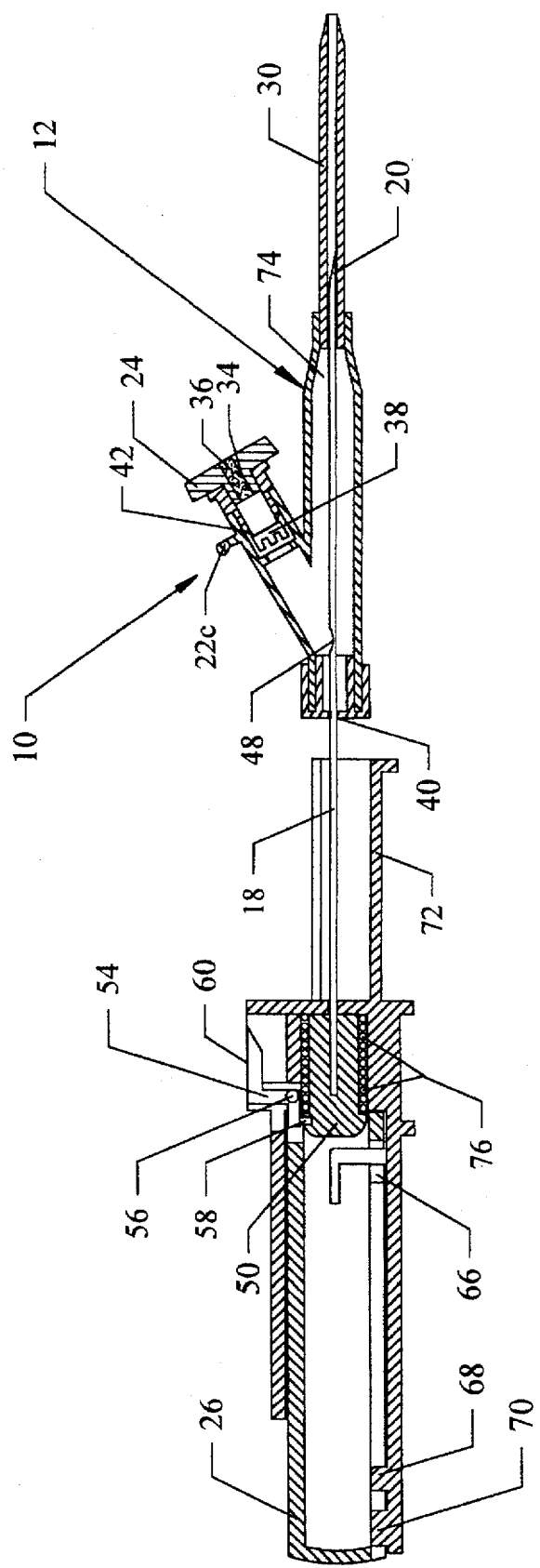
FIG. 14 illustrates a sectional view of the catheter being disengaged from the safety tube assembly with a telescoping tube of the catheter system; and, FIG. 15 illustrates a separated view of the catheter and the safety tube assembly with the engaged telescoping tube with the needle in a retracted position for disposal.
Figure 15:
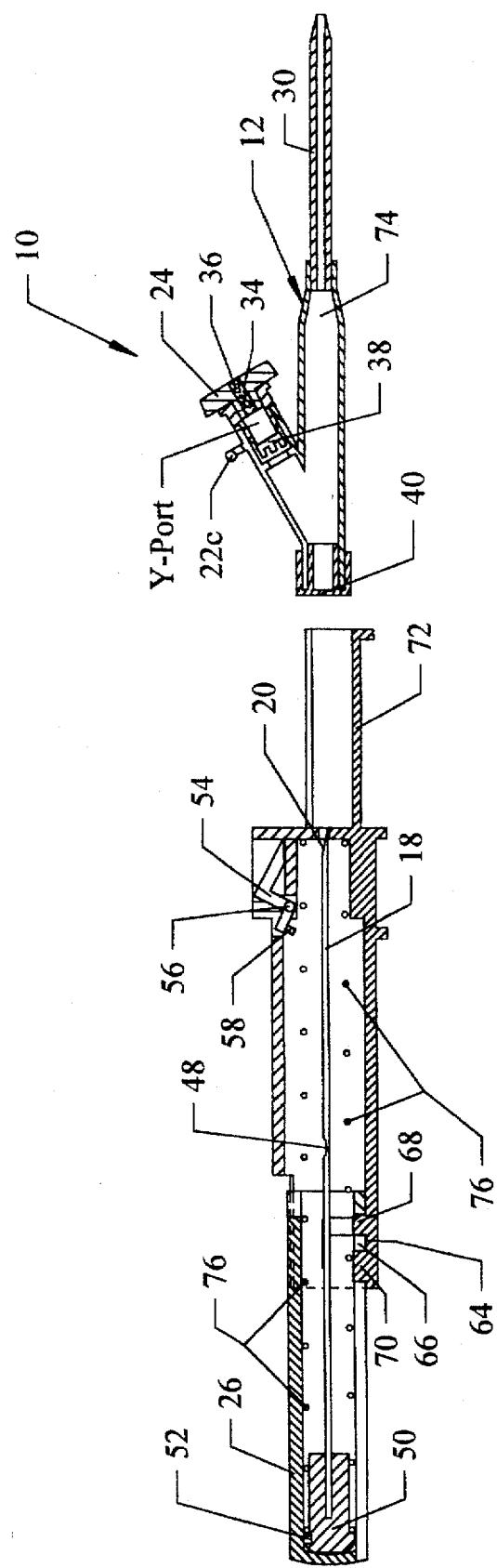

FIGS. 8, 14 and 15 particularly illustrate the mode of operation.

FIG. 8 illustrates the catheter system 10 as being pushed into a vein after the protection cap is removed.

FIG. 14 illustrates the disengagement of the safety tube assembly 16 from the catheter 12.

FIG. 15 illustrates the safety tube system 16 with the fully extended telescoping tube 26 and the needle 18 engaged within the telescoping tube 26 ready for disposal after actuation of the trigger 54 which occurs in during FIG. 14. The safety tube lock system contains the needle carrier with the needle as fully extended and ready for disposal. An IV can be inserted into Y-port after the vent cap is removed.

The catheter system operation occurs in the following order. All parts are pre-assembled in package. No assembly or rotation/manipulation of parts are required prior to IV start.

1. IV is removed from sterile package and protective needle cap removed.

2. The catheter is held at new optimized grip location (FIG. 1). Then piercing needle (FIGS. 1 and 3) is inserted into vein where a "pop" is then felt.

3. Blood then flows up piercing needle (FIG. 8), out new blood vent hole in approximate center of needle, then into new frontally located flash chamber (view is not obstructed by fingers or hands). Venting of displaced air is achieved by the new check valve; air will flow out of flash chamber through open check valve and out Y-port vented end cap (cap used to maintain sterility of Y-port opening).

4. Blood then deflects past rubber prepierced stopper, then routed up into Y-port, and finally reaching the check valve, hydraulic pressure from blood pushes check valve up against opposite valve seat opening (FIG. 2), sealing off any more flow of blood. The check valve in conjunction with rubber prepierced stopper effectively sealing flash chamber while still allowing venting of air.

5. When user easily (unobstructed view) sees this "flash," he can advance the catheter into vein by one of two methods; (a) user can hook optimized push flange (FIG. 1 or 10) (on either left or right side of hub) with thumbnail and advance catheter fully into vein (FIG. 13); (b) user can use index fingernail (FIG. 1 or 10) and advance catheter utilizing optimized push flange on upper portion of Y-port.

6. As catheter is advanced over needle (FIG. 14), flash chamber seal is still maintained by rubber prepierced resealable stopper.

7. User will then hold inserted catheter with one hand and hold telescoping safety tube unit with the other hand. Then depressing "trigger" (FIG. 14), will actuate lever that lifts pin out of hole in back of needle carrier, freeing spring and ejecting used needle into retracted telescoping safety tube. The tube will then be forced out to its fully extended length and locked in place utilizing locking system (FIGS. 10 and 15).

8. The safety tube can now be safely set down while user secures catheter to patient using tape.

9. Optionally, user can now inject lifesaving medications directly into rubber prepierced stopper, saving valuable time.

10. The user now has the option to decide if he would like to "Heparin Lock" the catheter or bloodlessly connect IV tubing to distal end of Y-port. This versatility allows the user to choose the method of use based on the situation.

11. If heparin locking is chosen, then user injects heparin into rubber prepierced stopper, flushing blood from catheter hub and eliminating possibility of blood clotting in hub chamber. IV start is now complete and done in half the time it normally takes, and user has not spilled a drop of blood.

12. If IV line attachment is chosen, then user can bloodlessly connect IV tubing to distal end of Y-port after optionally giving any emergency medications through rubber prepierced stopper (FIGS. 2 and 15); then tape IV line in place without loop. When IV is opened, the hydraulic pressure from IV fluid will push open the check valve in Y-port, allowing IV fluid to run around valve and into closed hub. The IV fluid will then flush out any latent blood from hub chamber and continue into patient. The Y-port design of the catheter eliminates the need to loop the connected IV tubing, eliminating possibility of "kinked" tubing, or chance that loop will catch on something and disconnect IV line.

13. Once IV line is secured in place, the protective telescoping safety tube assembly can be disposed of in proper "sharps" container.

14. If a blood sample is now required, all the user has to do is draw blood out of sealed flash chamber utilizing the rubber prepierced stopper. This eliminates need for second needle puncture and its associated risks.

15. If medications need to be given, they can be conveniently injected through rubber prepierced stopper (FIG. 2). The user is assured that he will be giving medicine through the shortest route conceivable for the most effective therapy possible.

16. After the IV start is complete, the catheter will continue to protect and serve the healthcare professional. If the IV line is accidentally set to low, the check valve in Y-port will prevent blood from backing up and clotting in IV line, saving the patient and user the need to start replacement IV. If the IV line becomes separated from catheter, there will not be any blood loss or contamination, as the check valve will prevent blood from escaping out of catheter. If the healthcare professional needs to switch Iv lines, he can do so quickly, safely, and without blood exposure, as check valve prevents blood back-flow. One can also "piggy-back" more than one IV drip as needed, preventing the need for second IV site to run second, third or more IV drips.

Various modifications can be made to the present invention without departing from the apparent scope hereof.

I claim:

1. A catheter assembly of the over-the-needle type for a user to percutaneously introduce a liquid into a bloodstream of a patient from a conduit, said catheter assembly comprising:

a catheter housing defining an interior region, a first port, and a second port, the conduit being operatively connected to said first port in fluid communication therewith such that the liquid may flow from the conduit into said interior region of said catheter housing;

a needle carried on said catheter housing and selectively removable therefrom, said needle having a proximal end and a distal end;

a catheter tube operatively connected to and extending from said catheter housing in covering relation to said needle, said catheter tube defining a lumen fluidly communicating with said interior region of said catheter housing and a distal end received within the bloodstream of the patient such that the fluid may flow from the interior of the catheter housing into the bloodstream of the patient;

a check valve operatively connected to said catheter housing and fluidly communicating with said first port, said check valve preventing blood or the liquid from flowing from said interior of said catheter housing out through said first port;

a self-sealing injection site connected to said catheter housing in sealing relation to said second port, said catheter housing, said check valve, and said self-sealing injection site forming a closed hub configuration external to the patient and to which the conduit is attached to introduce the liquid into the bloodstream of the patient, at least a portion of said needle extending through and being selectively removable front said self-sealing injection site and said catheter tube;

a safety tube assembly operatively connected to said catheter housing, at least a portion of said safety tube assembly being retractable relative to said catheter housing, said proximal end of said needle being operatively connected to said safety tube assembly such that when said portion of said safety tube assembly is retracted said distal end of said needle is completely withdrawn through said self-sealing injection site and received within said safety tube assembly;

a latching mechanism for engaging and maintaining said portion of said safety tube assembly which is retractible against rearward movement relative to said catheter housing, said latching mechanism including a trigger member which may be selectively actuated by the user; and a biasing mechanism for urging said portion of said safety tube assembly which is retractible rearwardly relative to said catheter housing, such that when the user selectively actuates said trigger member said latching mechanism releases said portion of said safety tube assembly such that it retracts and withdraws said distal end of said needle through said self-sealing injection site and completely into said safety tube assembly.

* * * * *